United States Patent [19]

Vogelstein et al.

[11] Patent Number: 5,750,352
[45] Date of Patent: May 12, 1998

[54] MONO-ALLELIC MUTATION ANALYSIS FOR IDENTIFYING GERMLINE MUTATIONS

[75] Inventors: Bert Vogelstein, Baltimore; Kenneth W. Kinzler, BelAir; Nickolas Papadopoulos, Baltimore, all of Md.

[73] Assignee: The Johns Hopkins University, Baltimore, Md.

[21] Appl. No.: 519,059

[22] Filed: Aug. 23, 1995

[51] Int. Cl.⁶ .......................... G01N 33/567; C12Q 1/68
[52] U.S. Cl. ................................ 435/7.21; 435/6
[58] Field of Search ................ 435/6, 7.1, 69.1, 435/7.21

[56] References Cited

PUBLICATIONS

Patterson et al., "Biochemical Genetic Analysis of Pyrimidine Biosynthesis in Mammalian Cells", *Somatic Cell Genetics* 3(5):483–495 (1977).

Wasmuth et al., "Linkage in Cultured Chinese Hamster Cells of Two Genes, emtB and leuS, involved in Protein Synthesis and Isolation of Cell Lines with Mutations in Three Linked Genes", *J. Cell Biol.* 87:697–701 (1980).

Acta Universitatis Oulvensis Sereia *Leila P* (214) 4–54 1990.

Mammalian Genome *Brown et al.* 5(7):434–437 (1994).

New England J. of Med. *Rustgi* 334(25):1694–1702 (1994).

Nature Genetics, *Ishioka et al.* 5: 124–129 (1993).

*Primary Examiner*—Eggerton A. Campbell
*Attorney, Agent, or Firm*—Banner & Witcoff, Ltd.

[57] ABSTRACT

A diagnostic strategy for detection of inherited diseases caused by germline mutations is based on somatic cell hybridization. Each allele of a human gene involved in the inherited disease is isolated in a somatic cell hybrid. The products of the isolated human allele are then observed in the absence of the other allele of the human.

19 Claims, 4 Drawing Sheets

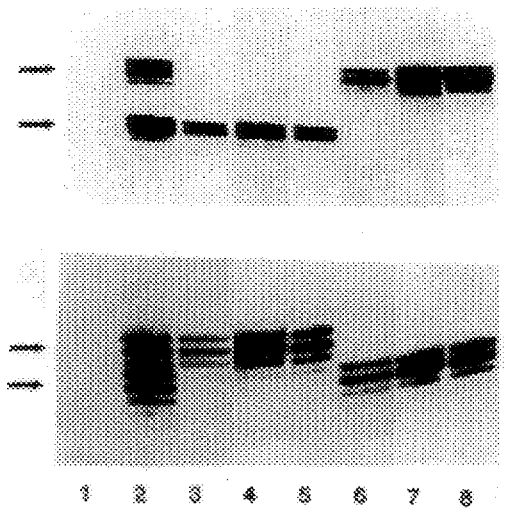
FIG. 2a
FIG. 2b
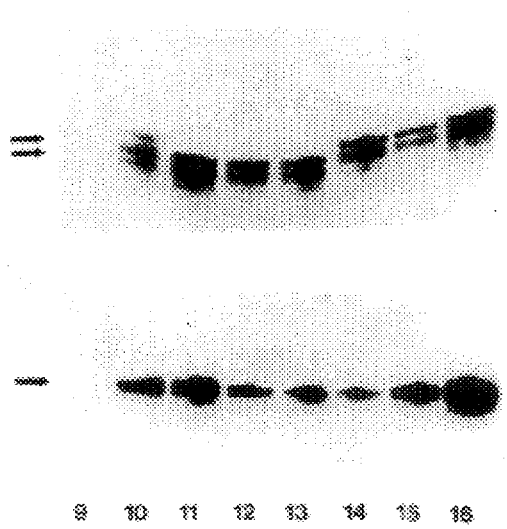
FIG. 2c
FIG. 2d

FIG. 3a
FIG. 3b
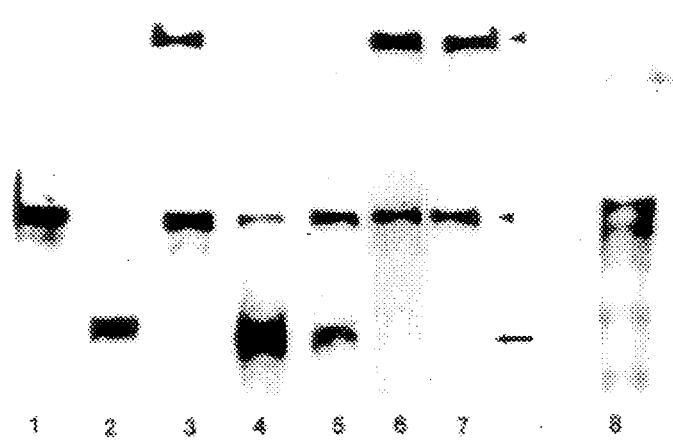
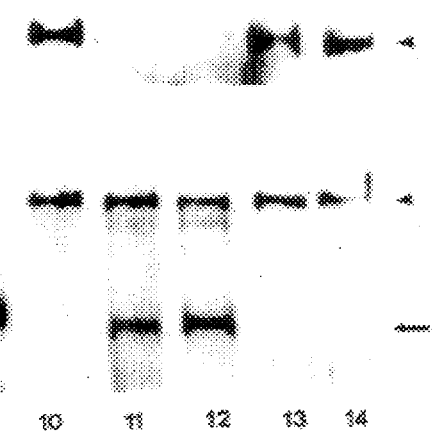
FIG. 3c
FIG. 3d

FIG. 4a
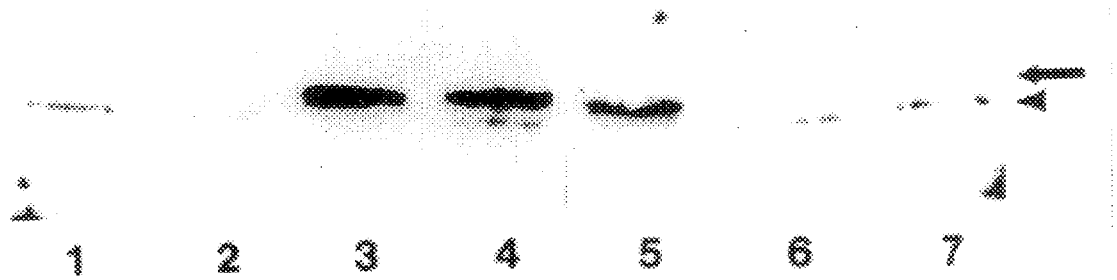
1  2  3  4  5  6  7
FIG. 4b
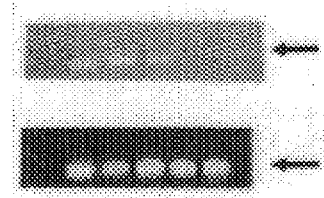
1 2 3 4 5 6
FIG. 4c

MONO-ALLELIC MUTATION ANALYSIS FOR IDENTIFYING GERMLINE MUTATIONS

This invention was supported with U.S. government funds, NIH grants CA35494 and CA62924. The government therefore retains certain rights in the invention.

BACKGROUND OF THE INVENTION

Dissection of germline mutations in a sensitive and specific manner presents a continuing challenge. In dominantly inherited diseases, mutations occur in only one allele and are often masked by the normal allele. For example, it is estimated that 20–40% of both APC and hMSH2 mutations are difficult or impossible to detect with standard techniques based on PCR analysis of genomic DNA or RNA transcripts[6–10]. Thus there is a need in the art for a technique which is relatively simple to perform and which will detect a broad spectrum of mutations in genes of clinical interest.

SUMMARY OF THE INVENTION

It is an object of the invention to provide a method for detecting mutations in the germline.

It is another object of the invention to provide a method for detecting mutations which are not detected by standard methods.

It is yet another object of the invention to provide a method for detecting mutations which lead to diminished or loss of expression of a gene product.

These and other objects of the invention are provided by one or more of the embodiments described below. In one embodiment a method of detecting mutations in a gene of interest on a chromosome of a human is provided. The method comprises the steps of:

obtaining cells of the human;

fusing said cells to rodent cell recipients to form a human-rodent cell hybrid;

testing said human-rodent cell hybrid to confirm the presence of said chromosome of the human in said hybrid;

testing said hybrid which contains said chromosome to detect a protein product of said gene, absence of said protein product or diminished amounts of said protein product indicating the presence of a mutation in the gene of interest of the human.

The present invention thus provides the art with a useful diagnostic tool in the evaluation of inherited diseases.

BRIEF DESCRIPTION OF THE DRAWINGS

FIGS. 2A–2D provides documentation of allele isolation in hybrids. Chromosome 2 hybrids were evaluated with the MSH2-distal marker YH5 (FIG. 2a) and the MSH2-proximal marker CA7 (FIG. 2b). DNA templates were from Urd-A hamster cells (lane 1), PBL from the normal donor (lane 2), hybrids containing one chromosome 2 allele (lanes 3–5), and hybrids containing the other (lanes 6–8). Chromosome 5 hybrids were evaluated with the APC-proximal marker LSCA (FIG. 2c) and the APC-distal marker D5S82 (FIG. 2d). DNA templates were from UCW56 hamster cells (lane 9), PBL from the normal donor (lane 10), hybrids containing one chromosome 5 allele (lanes 11–13), and hybrids containing the other allele (lanes 14–16). The PBL were homozygous for D5S82 (FIG. 2d), but heterozygous for LSCA (FIG. 2c). Note that to document retention of the relevant locus and alleles in the hybrids, only one of the two tested polymorphic markers need to be heterozygous in the patient.

FIGS. 3A–3D provides an analysis of chromosome 5 hybrids from FAP patients. Western blots were performed with the carboxyl-terminal specific IE-1 antibody (FIG. 3a and FIG. 3b), or amino-terminal specific FE-9 antibody (FIG. 3c and FIG. 3d). Proteins from the following cell lines were evaluated: UCW56 hamster cells (lanes 1,8), SW480, containing only a truncated APC protein (lanes 2 and 9), HCT116, containing only full length APC (lanes 3 and 10), hybrids containing allele 1 from patient P1 (lanes 4 and 5), hybrids containing allele 2 for patient P1 (lanes 6 and 7), hybrids containing allele 1 from patient P2 (lanes 11 and 12), and hybrids containing allele 2 from patient P2 (lanes 13 and 14). The FE-9, but not the IE-1 antibody recognizes the hamster APC protein. The arrows and arrowheads indicate truncated and full length APC proteins, respectively.

FIGS. 4A–4C shows an analysis of chromosome 2 hybrids from an HNPCC patient. FIG. 4a, Western blot of hMSH2. Lanes 1, 2, and 3 contain proteins from Urd-A, LoVo, and HCT116, respectively (see FIG. 3 legend). Lanes 4 and 5 contain proteins from hybrids containing the allele that is not linked to the disease in the patient's family, while lanes 6 and 7 show hybrids that contain the linked allele. The arrow indicates the full length hMSH2, and the arrowhead a non-specific band. FIG. 4b and FIG. 4c, PCR analysis of hMSH2 exons 1 and 16, respectively. The source of the DNA was hamster Urd-A cells (lane 1), parental lymphocytes (lane 2), hybrids containing the unlinked allele (lanes 3 and 4), and hybrids containing the linked allele (lanes 5 and 6). The arrows indicate the 260 and 160 bp PCR products of exon 1 and exon 16, respectively.

DETAILED DESCRIPTION OF THE PREFERRED EMBODIMENTS

Figure 1:
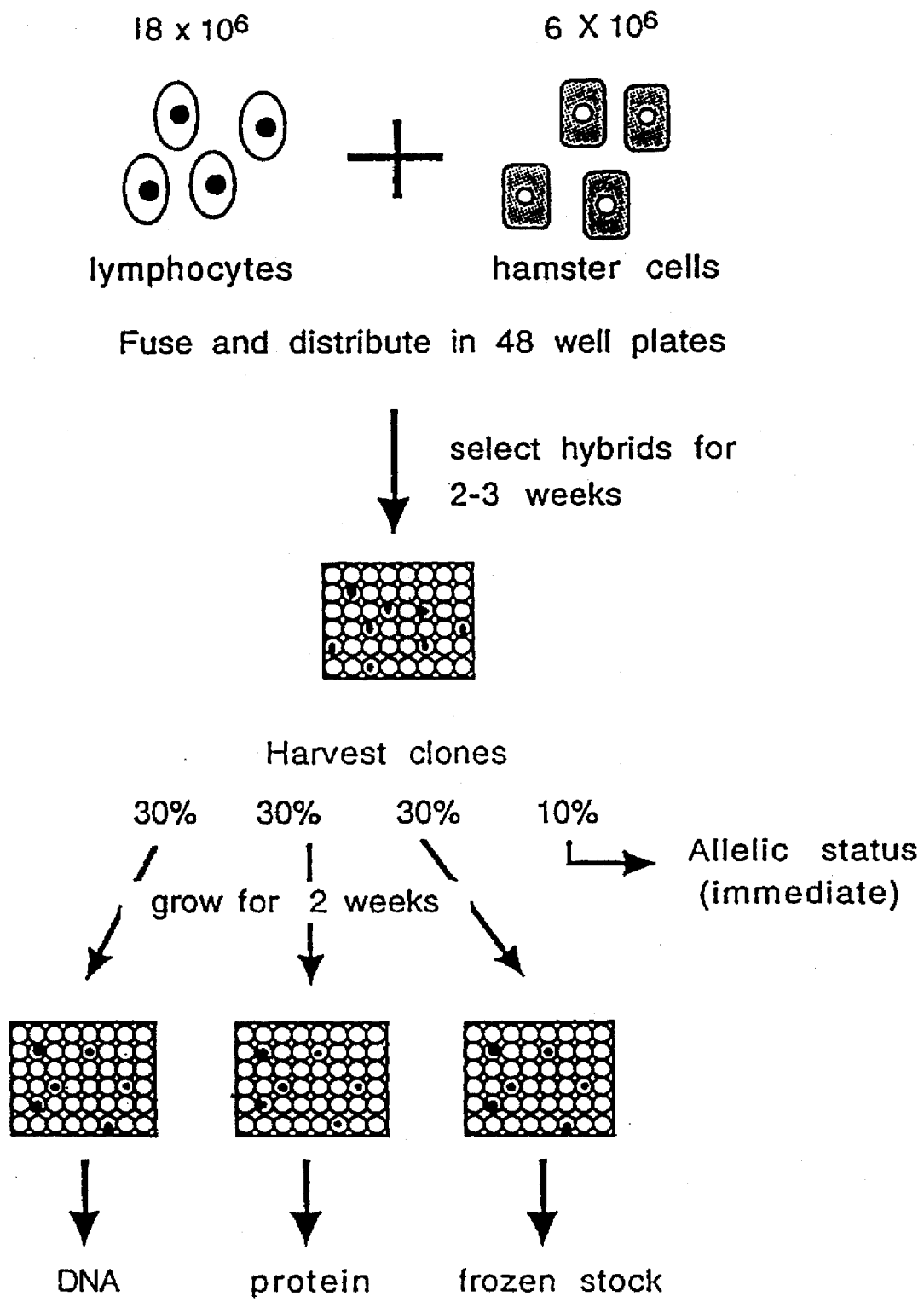
FIG. 1 is a schematic of the procedure for somatic cell hybrid generation.

It is a discovery of the present invention that human/rodent somatic cell hybrids can be reproducibly made using human cells which are routinely available in the clinical setting. Moreover, hybrids which contain just one of a particular human chromosome can be readily isolated. Analysis of the hybrids allows the observation of the product of a single human allele, without interference from the second allele's product which is present in human diploid cells. In addition, analysis of the hybrids allows identification of a haplotype which can be traced throughout the family of the individual to identify affected family members.

Genes of interest are typically those which have been found to be involved in inherited diseases. These include genes involved in colon cancer, breast cancer, Li-Fraumeni disease, cystic fibrosis, neurofibromatosis type 2, von Hippel-Lindau disease, as well as others. The identified genes include APC, merlin, CF, VHL, hMSH2, p53, hPMS2, hMLH1, BRAC1, as well as others. Mutations which can be identified include those in sequences that regulate transcription or translation, nonsense mutations, splice site alterations, translocations, deletions, and insertions, or any other changes that result in substantial reduction of the full-length protein. This method will likely not detect mutations that cause subtle alterations of a full-length (or nearly full-length) protein. However, these should be detectable by other methods, such as sequencing of RT-PCR products.

Cells of the human which may be used in fusions are any which can be readily fused to rodent cells. Peripheral blood lymphocytes (PBL) which are readily available clinical specimens, proved to be surprisingly good fusion partners, with or without prior mitogenetic stimulation, whether used fresh or stored for over one year at −80° C. Since inherited mutations are the subject of the present method, any cells of the human body can be used, since all such cells contain essentially the same genetic complement.

Rodent cell recipients for fusion preferably provide selection for specific human chromosomes. Thus, for example, rodent cells which are auxotrophic or biosynthetic mutants can be used. It is desirable that the human chromosome which carries the gene of interest also carry a gene which can complement the defect in the rodent cell. Thus growth under selective conditions will only yield hybrid cells which carry at least one of the human chromosomes which carry the gene of interest.

Fusion of cells according to the present invention can be accomplished according to any means known in the art. Known techniques for inducing fusion include polyethylene glycol-mediated fusion, Sendai virus-mediated fusion, and electrophoretic fusion. Cells can desirably be mixed at a ratio of between 10:1 and 1:10 human to rodent. Clones of fused cells generally become visible after about two to three weeks of growth.

Fused hybrid cells can be analyzed to determine that they do in fact carry a human chromosome which carries the gene of interest. Hybrid cells which have either of the two relevant human chromosomes can be distinguished from each other as well as from hybrids which contain both of the two human chromosomes. While any means known in the art for identifying the human chromosomes can be used, a facile analysis can be performed by assessing microsatellite markers proximal and distal to the gene of interest on the human chromosome. Such markers which are proximal and distal to the gene, are called herein "flanking markers". Such markers need not be immediately adjacent to the gene of interest. Other linked polymorphic markers can be used to identify the desired human chromosome in the hybrids.

Having achieved hybrid cells which contain one copy of the human gene of interest from the human who is being tested, mutation analysis can be performed on the hybrid cells. Mutations that result in reduced expression of the full-length gene product should be detectable by Western blotting using appropriate antibodies. Tests which rely on the function of the protein encoded by the gene of interest and enzyme assays can also be performed to detect mutations. Other immunological techniques can also be employed, as are known in the art.

If an immunological method is used to detect the protein product of the gene of interest in the hybrids, it is desirable that antibodies be used that do not cross-react with rodent proteins. Alternatively, the rodent genes which are homologous to the gene of interest can be inactivated by mutation to simplify the analysis of protein products. Such mutations can be achieved by targeted mutagenesis methods, as is well known in the art.

Functional tests can also be used to assess the normalcy of each allelic product. For example, if one inserted an expression construct comprising a β-galactosidase gene downstream from a p53 transcriptional activation site, into a rodent-human hybrid cell that contained human chromosome 17 but no endogenous p53, then one could detect mutations of the p53 on the human chromosome 17 by staining clones with X-gal. Other enzymatic or functional assays can be designed specifically tailored to the gene of interest.

It is a possibility that expression of the gene of interest might be inhibited in the hybrid cell environment. In order for the loss of expression of a gene of interest in the hybrid cells to be meaningfully interpreted as indicating a mutation in the human, one must confirm that the gene of interest, when wild-type, is expressed in rodent-human hybrid cells. This confirmation need not be done for each patient, but can be done once when the assay is being established.

When the assay of the present invention indicates that a mutation exists in the gene of interest, other family members can be tested to ascertain whether they too carry the mutation. Alternatively, the other family members can be tested to see if they carry the same chromosome as the affected family member. This can be determined by testing for a haplotype, i.e., a set of distinctive markers which are found on the chromosome carrying the mutation in the affected family member. Determination of a haplotype is a by-product of performing the assay of the invention on the first family member. When the hybrid cells are tested to confirm the presence of the relevant chromosome in the hybrid, for example by use of microsatellite markers, a distinctive marker set will be identified, which can then be used as a haplotype.

We report below the development of a sensitive and specific diagnostic strategy based on somatic cell hybridization termed MAMA (Mono-Allelic Mutation Analysis). We demonstrate the utility of this strategy in two different hereditary colorectal cancer syndromes[1], one caused by a defective tumor suppressor gene (APC in familial adenomatous polyposis, FAP) and the other caused by a defective mismatch repair gene (hMSH2 in hereditary non-polyposis colorectal cancer, HNPCC).

MAMA might considerably facilitate diagnosis of genetic disease. We estimate that 20–40% of both APC and hMSH2 mutations are difficult or impossible to detect with standard techniques based on PCR analysis of genomic DNA or RNA transcripts[6-10]. The analysis of the patient with HNPCC (FIG. 4) illustrates the potential advantages of MAMA in this regard, either alone or as an adjunct to PCR-based analyses.

MAMA has certain disadvantages as well. It requires approximately four to six weeks to complete the analysis. Genetic diagnostic tests are generally not emergency procedures, however, and sensitivity and specificity are far more important than immediacy in most circumstances. Though time consuming, MAMA is not labor intensive. Many alterations can be simply detected by a reduction of full length proteins upon Western blotting with appropriate antibodies. The only other mutations possible are those that cause subtle alterations of a full length (or nearly full length) protein. These should be detectable by automated sequencing of RT-PCR products derived from the monoallelic hybrids.

For the facile analysis of other hereditary diseases with MAMA, several practical criteria should be met. Rodent cell recipients should be available. Monoclonal antibodies that do not cross-react with hamster proteins simplify the analysis considerably. Not all gene products will be expressed in lymphocytes or in their derived somatic cell hybrids. Additionally, some mutations (e.g., tissue specific expression defect) may be difficult to detect with MAMA. The applicability of MAMA to any particular disease can only be confirmed by actual testing. Hamster fusion partners suitable for the analysis of other mismatch repair genes (on chromosomes 3 and 7) and other cancer predisposition syndromes (Li-Fraumeni, Neurofibromatosis, and hereditary breast cancer, all on chromosome 17) have been described[11–13] and should make extensions of MAMA to other diseases possible.

Finally, variations on MAMA are easy to envision. In particular, a functional test, rather than a sequence-based test, could be used to assess the normalcy of each allelic product[14]. In some cases, homologous recombination could be used to remove the endogenous hamster gene and thereby facilitate such functional analyses. As an example, consider p53 in the Li-Fraumeni syndrome. In a hamster cell hybrid with no endogenous p53, a β-galactosidase gene placed downstream of a p53 transcriptional activation site[14,15] could be used to detect mutations simply by staining clones with X-gal.

EXAMPLES

EXAMPLE 1

This example demonstrates the development of a simple scheme for producing somatic cell hybrids from routinely available clinical samples such as peripheral blood lymphocytes (PBL).

Cells. The Urd-A cell line[16] was grown in F-12 supplemented with 10%(v/v) dialyzed fetal calf serum and 30 mM uridine at 37° C. The UCW56 cell line[17] was grown in Dulbeco's Modified Eagles medium (DMEM) supplemented with 10%(v/v) fetal calf serum (FCS) at 32° C. Lymphoblastoid lines were grown in RPMI 1640 supplemented with 10%(v/v) FCS. Peripheral blood lymphocytes (PBL) were isolated with Histopaque 1077 (Sigma) according to the manufacturer's protocol. The cells were used immediately for fusions, or resuspended in RPMI 1640/10% FCS, with or without 10 mg/ml PHA and 50 U/ml IL2, and incubated at 37° C. overnight. Alternatively, Histopaque isolated PBL were frozen at −80° C. in RPMI 1640/10% FCS containing 10% DMSO.

Isolation of somatic cell hybrids. The following protocol was derived after testing numerous parameters, including the number and concentration of each cell type, pre-stimulation of PBL with mitogens (which had no effect), and the distribution of cells following fusion. In addition to freshly isolated PBL, it was found that PBL frozen at −80° C. as described above could also be productively fused immediately upon thawing at 37° C. Human cells ($18 \times 10^6$) and hamster cells ($6 \times 10^6$) were mixed, aliquoted into two 15 ml conical tubes, and collected by centrifugation at room temperature (RT) at 200 g. The cell pellets were each resuspended in 10 ml DMEM without serum, and the cells were collected once more by centrifugation. The media was aspirated carefully until the pellets were almost dry. The cell pellets were loosened by tapping the tube and 1 ml of 50% PEG in phosphate buffered saline (Sigma) was added to each tube slowly. The cells were allowed to fuse for 1 minute at RT, and fusion terminated by the addition of 10 ml DMEM. The cells from each tube were collected by centrifugation, resuspended in 96 ml of the appropriate medium, and distributed into two 48 well plates (Costar). Selection started two days later. Selection against unfused human lymphocytes was based on the fact that these cells do not attach to plastic. Unfused hamster cells were selected against by growth in Ham's F12/10% FCS at 37° C. for chromosome 2 hybrids and in DMEM/10% FCS at 39° C. for chromosome 5 hybrids. The Urd-A cell line has a defect in de novo pyrimidine synthesis[16], and will not grow in medium without uridine in the absence of a chromosome 2 gene contributed by the human fusion partner. Similarly, the UCW56 hamster cells have a temperature sensitive mutation required for protein synthesis[17], and will not proliferate at 39° C. in the absence of chromosome 5 genes contributed by the human fusion partner. The medium was replenished every three days. Two to three weeks later, wells containing visible clones were harvested by trypsinization. One tenth was used for DNA (see below), and the remainder split into three wells each in separate 48 well plate, one devoted to DNA analysis, one to protein analysis, and one for creating frozen stocks.

Results. Numerous parameters were evaluated in an effort to optimize lymphoblastoid-hamster fusions, first with EBV-transformed lymphoblastoid cells (as a reproducible control), then with PBL. A diagram of the optimized procedure is depicted in FIG. 1. PBL and hamster cells were mixed at an appropriate ratio, exposed to PEG, and then distributed into 48 well plates under conditions which selected for fused cells. Clones became visible in two to three weeks, at which time they were harvested, a portion analyzed for allele content, and the rest divided into three wells each in a separate 48 well plate. Approximately two weeks later, the wells were harvested, one used for protein analysis, the second for nucleic acid analysis, and the third for generation of a frozen stock. Typically, fusion of $18 \times 10^6$ PBL with $6 \times 10^6$ hamster cells generated an average of 16 hybrids (range 8–30).

EXAMPLE 2

This example demonstrates that single alleles were isolated in the somatic cell hybrid clones.

DNA analysis. Confluent cells in 48 well plates were washed with Hank's balanced salt solution, and 100 ml of proteinase K (100 mg/ml) in TE 10 (10 mM Tris [pH 8.0], 1 mM EDTA) were added to each well. The plates were incubated for 2 hr at 58° C. The liquid was transferred to 1.5 ml tubes and boiled for 5 minutes. Cells growing in suspension were collected by centrifugation, and DNA was prepared similarly, except that the 58° C. incubation was performed in 1.5 ml tubes. Two ml of each DNA sample were used for each PCR reaction. The microsatellite markers used for chromosome 2 were YH5 and CA7[4,18], and for chromosome 5 were D5S82[19] and LSCA[20]. The PCR reactions were carried out in 96 well plates with end-labelled primers in 10 ml reactions in PCR Master Mix (Boehringer Mannheim), by heating to 95° C. for 30 seconds, 50° C for 1 minute, 70° C. for 1 minute for 32 cycles, then 70° C. for 5 minutes for 1 cycle. The PCR products were separated on 6% denaturing polyacrylamide gels and visualized by autoradiography. Amplification of exons 1, 2,3, 12, and 16 of hMSH2 was performed as described previously[21].

Results. Microsatellite markers[3,4] proximal and distal to the gene of interest were assessed. Of 83 chromosome 5-derived hybrids generated with lymphocytes from a normal individual, 32 contained one allele, 33 contained the other allele, and 18 contained both alleles. Of 20 chromosome 2-derived hybrids analyzed, 9 contained one allele, 7 contained the second allele, and 4 contained both alleles. The hybrids containing two alleles could be passaged for two more weeks if desired, by which time they generally lost one allele (3 of 3 hybrids tested). Examples of microsatellite assays are shown in FIG. 2. Every tested hybrid contained both the proximal and distal microsatellite markers, indicating that the entire gene of interest was present in each hybrid.

EXAMPLE 3

This example demonstrates that mutations that result in greatly reduced expression of the full length gene product are detectable by Western blotting of hybrid proteins using appropriate antibodies.

Western blot analysis. Cells were resuspended in buffer composed of 0.0625M Tris (pH 6.8), 5% beta-mercaptoethanol, 2% SDS, 10% glycerol, /0.025% bromophenol blue, and quantitated according to previously published methods[22]. Western blot analysis for APC was carried out according to ref. 23. Briefly, proteins were separated by electrophoresis in 3% low melting point agarose gels and transferred to polyvinyldifluoride membranes (Immobilon; Millipore) by capillary action in TBS (100 mM Tris, 150 mM NaCl) containing 0.05% SDS. These membranes were treated as described below. For hMSH2, proteins were separated on 10% polyacrylamide/SDS gels, and transferred to polyvinyldifluoride membranes for 1 hr in 40 mM glycine, 48 mM Tris, 0.0375% SDS buffer using a semi-dry electroblotter (ISS). The membranes were rinsed in TBS and blocked in TBS containing 10% nonfat dried milk and 0. 1% Tween-20, for 1.5 hr. After incubation with the primary antibody at 1 mg/ml in TBS containing 5% nonfat dried milk and 0.1% Tween-20 for 2 hr, the filters were washed multiple times with TBS containing 0.1% Tween-20 (TBST) for 30 minutes. Horseradish peroxidase-conjugated goat anti-mouse antibody was then applied to the membranes for 1 hr in TBST. The membranes were then washed 6 times with TBST for total of 1 hr. Peroxidase activity was detected using Amersham's ECL following the manufacturer's protocol. Methods used for production of anti-APC and anti-hMSH2 antibodies are described in ref. 23 and 24.

Results. We evaluated two FAP patients with previously identified mutations of APC. In each case, six hybrids from each patient were selected for analysis, three with the maternal allele and three with the paternal. Western blot analysis was performed with monoclonal antibody IE-1, which recognizes the C-terminus of human APC but does not recognize hamster APC. This antibody demonstrated that both patients had abnormalities of APC confined to one allele. No full length APC protein was found in hybrids containing allele 1 of either patients P1 or P2, while full length APC proteins were expressed in the other hybrids (examples in FIG. 3a, b).

These results document an abnormality that would be adequate for most diagnostic purposes. Other members of the family could be analyzed by the same techniques or assessed for the presence of the affected haplotype, revealed as a by-product of the hybrid analysis (FIG. 2). For research purposes, however, it is often useful to define the precise mechanisms underlying the abnormality. Western blots using mAb FE-9, recognizing the amino-terminus of APC, revealed truncated products of 157 and 145 kD in hybrids containing the mutant alleles of patients P1 (FIG. 3c) and P2 (FIG. 3d), respectively. These truncations were consistent with sequence data which demonstrated frameshift mutations at codons 1309 and 1211 in patients P1 and P2, respectively (data not shown).

EXAMPLE 4

This example demonstrates the use of MAMA for analysis of mutations which were impossible to detect with standard methods.

We selected a kindred in which colorectal cancer incidence was tightly linked (LOD score>3.0) to inheritance of markers on chromosome 2p16[5]. A patient from this kindred had been evaluated for mutations of hMSH2 by IVSP[6,7], by RT-PCR and sequence analysis of the entire coding region, and by Western and Southern blot analysis, with no evidence of mutation. However, an abnormality was unambiguously observed upon MAMA: no hMSH2 polypeptides were found in hybrids containing allele 1, the allele linked to the disease in this kindred (FIG. 4a).

To determine the mechanism underlying the abnormality, PCR analysis of individual exons was performed with hybrid DNA. Exon 1 could not be amplified from hybrids containing allele 1 using several primer pairs (FIG. 4b, lanes 5 and 6), but could be amplified from hybrids containing allele 2 (FIG. 4b, lanes 3 and 4). Exons 2, 3, 12, and 16 could be amplified from all hybrids (examples in FIG. 4c). Thus, the mutation in this kindred likely resulted from a deletion that included the 5' end of the gene. This deletion was not apparent in PCR analysis of DNA from the parental PBL, which revealed only the wild type allele (FIG. 4b, lane 2).

References

1. Rustgi, A. K. Hereditary gastrointestinal polyposis and nonpolyposis syndromes. *New Engl. J. Medicine* 331, 1694–1702 (1994).
2. Groden, J., et al. Identification and characterization of the familial adenomatous polyposis coli gene. *Cell* 66, 589–600 (1991).
3. Weber, J. L., and May, P. E. Abundant class of human DNA polymorphism which can be typed using the polymerase chain reaction. *Am J. Hum Genetics* 44, 388–396 (1989).
4. Gyapay, G., et al., The 1993–94 Genethon human genetic linkage map. *Nature Genetics* 7, 246–339 (1994).
5. Nystrom-Lathi, M. et al. Mismatch repair genes on chromosome 2p and 3p account for a major share of hereditary nonpolyposis colorectal cancer families evaluable by linkage. *Amer. J. Hum. Gen.* 55, 659–665 (1994).
6. Powell, S. M., et al. Molecular diagnosis of familial adenomatous polyposis. *New Engl J Med* 329, 1982–1987 (1994).
7. Roest, P. A. M., Roberts, R. G., Sugino, S., van Ommen, G. B., Dunnen, J. T. Protein truncation test (PTT) for rapid detection of translation-terminating mutations. *Hum. Mol. Gen.* 2, 1719–1721 (1993).
8. Orita, M., Iwahana, H., Kanazawa, H., Hayashi, K., and Sekiya, T. Detection of polymorphisms of human DNA by gel electrophoresis as single-strand conformation polymorphisms. *Proc. Natl. Acad. Sci. U.S.A.* 86, 2766–2770 (1989).
9. Myers, R., M., Maniatis, T., and Lerman, L. S. Detection and localization of single base changes by denaturing gradient gel electrophoresis. *Meth. Enzymol.* 155, 501–527 (1987).
10. Cotton, R. G. H. Current methods of mutation detection. *Mut. Res.* 285, 125–144 (1993).
11. Patterson, D., Jones, C., Morse, H., Rumsby, P., Miller, Y., and Davis, R. Structural gene coding for multifunctional protein carrying orotate phosphoribosyltransferase and OMP decarboxylase activity is located on long arm of human chromosome 3. *Somatic Cell Genetics* 9, 359–374, 1983.
12. Arfin, S. M., Cirullo, R. E., Arredondo-Vega, F. X., and Smith, M. Assignment of structural gene for asparagine synthetase to human chromosome 7. *Somatic Cell Genetics* 9, 517–531, 1983.
13. Talavera, A., and Basilico, C. Temperature sensitive mutants of BHK cells affected in cell cycle progression. *J. Cell. Physiol.* 92, 425–536, 1977.

14. Ishioka, C., et al. Screening patients for heterozygous p53 mutations using a functional assay in yeast. *Nature Genetics* 5, 124–129 (1993).

15. Vogelstein, B. and Kinzler, K. W. p53 function and dysfunction. *Cell* 70, 523–528 (1992).

16. Patterson, D., and Carnright, D., V. Biochemical genetic analysis of pyrimidine biosynthesis in mammalian cells: I. Isolation of a mutant defective in the early steps of de novo pyrimidine synthesis. *Somatic Cell Genetics* 3, 483–495 (1977).

17. Wasmuth, J. J., and Chu, L.-Y. Linkage in cultured chinese hamster cells of two genes, emtB and leuS, involved in protein synthesis and isolation of cell lines with mutations in three linked genes. *J. Cell Biol.* 87, 697–702 (1980).

18. Leach, F., et al. Mutations of a mutS homolog in hereditary non-polyposis colorectal cancers. *Cell* 75, 1215–1225 (1993).

19. Breukel, C., et al. CA repeat polymorphic at the D5S82 locus, proximal to APC. *Nucleic Acids Research* 19, 5804 (1991).

20. Spirio, L., Joslyn, G., Nelson, L., Leppert, M., White, R. A CA repeat 30–70 kb downstream from the adenomatous polyposis coli (APC) gene. *Nucleic Acids Research* 19, 6348 (1991).

21. Liu, B. et al. hMSH2 mutations in Hereditary Nonpolyposis Colorectal Cancer kindreds. *Cancer Research* 54, 4590–4594 (1994).

22. Soedjak, H. S. Colorimetric micromethod for protein determination with erythrosin B. *Anal. Biochem.* 220, 142–148 (1994).

23. Smith, K. et al. The APC gene product in normal and tumor cells. *Proc. Natl. Acad. Sci. U.S.A.* 90, 2846–2850 (1993).

24. Leach, F., Hill, D., Kinzler, K. W., Vogelstein, B. submitted for publication (1995).

We claim:

1. A method of detecting mutations in a first gene of a human, wherein the first gene has been previously mapped to a human chromosome, comprising the steps of:

obtaining cells of the human;

fusing said cells to rodent cell recipients which carry a mutation which can be complemented by a second gene which has been mapped to said chromosome, to form human-rodent cell hybrids;

testing said human-rodent cell hybrids to confirm the presence of said chromosome of the human in said hybrid;

testing said hybrids which contains said chromosome to detect a protein product of said first gene, absence of said protein product or diminished amounts of said protein product indicating the presence of a mutation in the first gene of the human.

2. The method of claim 1 wherein the first gene is APC.

3. The method of claim 1 wherein the first gene is hMSH2.

4. The method of claim 1 wherein the first gene is p53.

5. The method of claim 1 wherein the rodent cell recipients are auxotrophic mutants.

6. The method of claim 1 wherein the rodent cell recipients are biosynthetic mutants.

7. The method of claim 1 wherein the cells of the human are peripheral blood lymphocytes.

8. The method of claim 1 wherein the fusion is performed in the presence of polyethylene glycol.

9. The method of claim 1 wherein the fusion is electrophoretic.

10. The method of claim 1 wherein the presence of said chromosome is tested by identifying the presence of microsatellite markers flanking the first gene.

11. The method of claim 1 wherein said step of testing to detect a protein product is performed by Western blotting.

12. The method of claim 1 wherein said step of testing to detect a protein product is performed by an enzyme reaction.

13. The method of claim 1 wherein said step of testing to detect a protein product is performed by assaying for function of the protein product.

14. The method of claim 11 wherein an antibody which is specifically immunoreactive with the protein product of the first gene is used in the Western blotting, wherein said antibody is not immunoreactive with a homologous protein product of the rodent cell.

15. The method of claim 1 further comprising the step of:

testing a human-rodent cell hybrid which contains a wild-type allele of the first gene, to confirm that said allele can be expressed in human-rodent cell hybrids.

16. The method of claim 13 wherein one or more rodent protein product homologues of the human protein product of the gene of interest are inactivated by mutation.

17. The method of claim 1 further comprising the step of:

if a mutation in the first gene of the human is indicated, determining a haplotype for the chromosome of the human; and testing one or more family members for the presence of said haplotype, wherein the presence of said haplotype implies the presence of the mutation.

18. The method of claim 17 wherein the haplotype comprises an allele of each of at least two microsatellite markers flanking said first gene.

19. A method of detecting mutations in a first gene of a human, wherein the first gene has been previously mapped to a human chromosome, comprising the steps of:

obtaining peripheral blood lymphocytes of the human;

fusing said peripheral blood lymphocytes to rodent cell recipients which carry a mutation which can be complemented by a second gene which has been mapped to said chromosome, to form human-rodent cell hybrids;

testing said human-rodent cell hybrids to confirm the presence of said chromosome of the human in said hybrids, wherein the presence of said chromosome is tested by identifying the presence of microsatellite markers flanking the first gene;

testing said hybrids which contains said chromosome to detect a protein product of said first gene by Western blotting, absence of said protein product or diminished amounts of said protein product indicating the presence of a mutation in the first gene of the human.

* * * * *